(12) United States Patent
Wortzman et al.

(10) Patent No.: US 7,025,977 B2
(45) Date of Patent: Apr. 11, 2006

(54) COMPOSITIONS FOR THE TREATMENT OF PIGMENTATION DISORDERS AND METHODS FOR THEIR MANUFACTURE

(75) Inventors: Mitchell Wortzman, Scottsdale, AZ (US); Philip J. Gordon, Plano, TX (US); Eugene H. Gans, Scottsdale, AZ (US); Bhiku G. Patel, Chandler, AZ (US)

(73) Assignee: Medicis Pharmaceutical Corporation, Scottsdale, AZ (US)

( * ) Notice: Subject to any disclaimer, the term of this patent is extended or adjusted under 35 U.S.C. 154(b) by 283 days.

(21) Appl. No.: 10/616,778

(22) Filed: Jul. 10, 2003

(65) Prior Publication Data

US 2004/0028627 A1 Feb. 12, 2004

Related U.S. Application Data

(62) Division of application No. 09/864,083, filed on May 23, 2001.

(51) Int. Cl.
*A61K 7/42* (2006.01)

(52) U.S. Cl. .................. 424/401; 424/59; 514/844
(58) Field of Classification Search ............... 424/401, 424/402, 59; 514/844, 947
See application file for complete search history.

(56) References Cited

U.S. PATENT DOCUMENTS 5,932,612 A * 8/1999 Gordon et al. ............. 514/458

* cited by examiner

*Primary Examiner*—Thurman K. Page
*Assistant Examiner*—Sharon Howard
(74) *Attorney, Agent, or Firm*—William J. McNichol, Jr.; Maryellen Feehery; Reed Smith LLP

(57) ABSTRACT

The present invention addresses the problem of excessive discoloration in hydroquinone compositions of a neutral pH. Antioxidants in the hydroquinone phase and inorganic or amino acyl cationic salts of acidic ascorbyl esters, preferably sodium metabisulfite and magnesium ascorbyl phosphate respectively, are effective in stabilizing such hydroquinone compositions, which are used in treatment of pigmentation disorders. Protected retinoid may be added to these compositions for additional skin benefit effects.

23 Claims, No Drawings

COMPOSITIONS FOR THE TREATMENT OF PIGMENTATION DISORDERS AND METHODS FOR THEIR MANUFACTURE

CROSS REFERENCE TO RELATED APPLICATIONS

This application is a divisional of U.S. Ser. No. 09/864,083, filed May 23, 2001.

FIELD OF THE INVENTION

This invention relates to methods and compositions for the treatment of pigmentation disorders, including hyperpigmentation and vitiligo.

BACKGROUND OF THE INVENTION

Pigmentation disorders can take a variety of forms like hyperpigmentation and hypopigmentation, such as melasma (dark patches experienced in pregnancy), liver spots (which often develop with age), as a side effect of birth control pills, and as a persistent result of acne, burns, bites and other skin injuries, and vitiligo.

In the United States, the most commonly used treatment for hyperpigmentation is 1,4-benzenediol, which is known as hydroquinone. Treatment with hydroquinone interferes with the action of tyrosinase, which is an enzyme used in the synthesis of melanin, and compositions are sold across the counter at about 2% hydroquinone and by prescription at higher concentrations.

Hydroquinone compositions are effective but have some undesirable side effects. These can be burning, redness, sensitization and irritation in some patients.

Additionally, the hydroquinone compositions frequently discolor over time and turn from a whitish color to a brown or even black. Without being limited to the mechanism of this discoloration, it is believed that the discoloration may be caused at least in part by oxidation of the hydroquinone. Discoloration of hydroquinone compositions may be accelerated by repeated exposure to oxygen or exposing the compositions to high temperatures, which may be found inside a car or delivery vehicle on a hot sunny day.

The natural pH for conventional hydroquinone compositions is acidic, generally less than about 4 even though this is harsh to the skin and to other components of the product. This range of pH has been preferred for hydroquinone compositions, because it has been believed that the hydroquinone is less likely to excessively discolor under acid conditions. Variations in pH have proven to result in excessive discoloration ranging from brownish to black. The present invention combats this problem, with hydroquinone compositions in the neutral pH range, preferably a pH of from about 5.5 to about 8.0, more preferably a pH of from about 5.5 to about 7.5, and most preferably at a pH of from about 6.0 to about 7.5.

Some hydroquinone compositions include antioxidants, such as ascorbyl palmitate. Other antioxidants, for example cationic salts of acidic ascorbyl esters, most preferably magnesium ascorbyl phosphate, aminopropyl ascorbyl phosphate, and sodium ascorbyl phosphate, have not been utilized in combination with hydroquinone in view of the acidic pH, generally from about 3.4 to about 3.5, and the recommended pH range for magnesium ascorbyl phosphate is about 7.0 to 8.5. However, hydroquinone discolors at the pH range of 7.0 to 8.5. Thus, while cationic salts of acidic ascorbyl esters, preferably magnesium ascorbyl phosphate and aminopropyl ascorbyl phosphate, have beneficial antioxidant effects on the skin, the combination with hydroquinone in the invention results in a compatible and stable composition.

Antioxidants, preferably sulfites, including but not limited to sulfites, bisulfites, metabisulfites, their salts, and their derivatives, most preferably sodium metabisulfite, have been used to stabilize certain compositions, which have included hydroquinone. Since hydroquinone has a tendency to discolor through oxidation, these antioxidants are used because they have greater tendencies to oxidize than hydroquinone. Sodium metabisulfite has the added advantage that it does not discolor by oxidation. In hydroquinone and sodium metabisulfite compositions, it is believed that the sodium metabisulfite oxidizes first and delays the start of any oxidation of the hydroquinone, so that excessive discoloration is delayed or totally avoided. However, these hydroquinone-containing compositions were in the acidic pH range and did not contain cationic salts of acidic ascorbyl esters, such as magnesium ascorbyl phosphate.

While patients suffer from pigmentation disorders, they may also suffer from other skin disorders and signs of aging, including but not limited to rough skin texture, mottled pigmentation, sallow complexion, lines and wrinkles. Retinoid compositions, in particular retinoic acid, retinal, and their derivatives, isomers and analogs (such as adapalene, tazarotene and isotretoin) are known to be effective in improving rough skin texture, mottled pigmentation, sallow complexion, lines and wrinkles.

It would be desirable to combine the pigmentation disorder treatment with this skin benefit ingredient in one composition. However, a problem with a formulation containing both retinoids and hydroquinone has been their incompatible pH ranges. Thus, merely adding one retinoid to a hydroquinone composition would result in instability and/or discoloration, and adding hydroquinone to a retinoid product would have a similar result.

SUMMARY OF THE INVENTION

This invention addresses the problem of formulating a pigmentation disorder treatment composition with hydroquinone without an excessive discoloration of the composition in the pH range of about 7.0. We have discovered that a hydroquinone composition (with about 1 to about 12% hydroquinone, preferably with about 2% to about 10%, more preferably with about 2% to about 8%, more preferably with about 2% to about 4%, most preferably with about 3% to about 4% hydroquinone) with preferably a pH of from about 5.5 to about 8.0, more preferably a pH of from about 5.5 to about 7.5, and most preferably at a pH of from about 6.0 to about 7.5, can include cationic salts of acidic ascorbyl esters, preferably sodium ascorbyl phosphate, more preferably aminopropyl ascorbyl phosphate, most preferably magnesium ascorbyl phosphate as an antioxidant and the color destabilization problems are appreciably less as compared to hydroquinone compositions without such a cationic salt of acidic ascorbyl esters in the neutral pH range: preferably a pH of from about 5.5 to about 8.0, more preferably a pH of from about 5.5 to about 7.5, and most preferably at a pH of from about 6.0 to about 7.5.

Additionally, a water-soluble antioxidant, preferably a sulfite, including but not limited to sulfites, bisulfites, metabisulfites, their salts and their derivatives, most preferably sodium metabisulfite, may be helpful in stabilizing the hydroquinone composition. Most preferably, when both a water-soluble antioxidant, preferably sulfite, including but not limited to sulfites, bisulfites, metabisulfites, their salts and their derivatives, most preferably sodium metabisulfite, and a cationic salt of acidic ascorbyl esters, most preferably magnesium ascorbyl phosphate, are present, the color of the hydroquinone composition is stabilized in the neutral pH range, preferably for greater than about six months, more preferably for greater than about twelve months and most preferably for greater than about eighteen months.

Since the neutral pH of the hydroquinone composition with sodium metabisulfite and magnesium ascorbyl phosphate is preferably from about 5.5 to about 8.0, more preferably a pH of from about 5.5 to about 7.5, and most preferably at a pH of from about 6.0 to about 7.5, the pH is acceptable for also including retinoids in the composition.

Unfortunately, retinoids, in particular retinoic acid, retinal, and their derivatives, isomers and analogs (such as adapalene, tazarotene and isotretoin) also have discoloration problems due to oxidation. Forms of retinoids have been developed wherein the retinoid is protected by a protective system. The protective system can be an entrapment system, a single or multi-laminar system, such as by the formation of vesicles such as a liposome or by utilizing wax, paraffin, silicone, polyethylene, or any material or system which protects the retinoid from oxidation. The preferred protected retinoid is in the form of small beads or vesicles which are of a form that can be adjusted to be incorporated into varied topical compositions.

Retinoids, in particular retinoic acid, retinal, and their derivatives, isomers and analogs (such as adapalene, tazarotene and isotretoin), which are protected have been shown to also be color stable in hydroquinone, magnesium ascorbyl phosphate and sodium metabisulfite composition at about a neutral pH, preferably from about 5.5 to about 8.0, more preferably from about 5.5 to about 7.5, and most preferably from about 6.0 to about 7.5. Retinoids are included in the invention from about 0.01 to about 5%, preferably from about 0.025% to about 2.0%, more preferably from about 0.05% to about 1%, and most preferably from about 0.025% to about 0.5%.

A further embodiment of the invention includes a method for stabilizing a hydroquinone composition (with about 1% to about 12% hydroquinone, preferably about 2% to about 10%, more preferably about 2% to about 8%, and most preferably about 3% to about 4%) with a neutral pH of from about 5.5 to about 8.0, more preferably a pH of from about 5.5 to about 7.5, and most preferably at a pH of from about 6.0 to about 7.5, by adding a water-soluble antioxidant, preferably sulfite, including but not limited to sulfites, bisulfites, metabisulfites, their salts and their derivatives, most preferably sodium metabisulfite, and a cationic salt of acidic ascorbyl esters, preferably sodium ascorbyl phosphate, more preferably aminopropyl ascorbyl phosphate, most preferably magnesium ascorbyl phosphate. Protected retinoid, with its skin benefit capabilities, may also be included with the hydroquinone composition.

DETAILED DESCRIPTION OF THE PREFERRED EMBODIMENTS

The present invention is not to be limited by any mechanism described in the specification, because it is defined by the claims.

One embodiment of the invention is a composition which comprises hydroquinone (about 1% to about 12%, preferably about 2% to about 10%, more preferably about 2% to about 8%, more preferably with about 2% to about 4%, and most preferably about 3% to about 4%) and has a neutral pH of from about 5.5 to about 8.0, more preferably a pH of from about 5.5 to about 7.5, and most preferably at a pH of from about 6.0 to about 7.5. This composition is color stabilized and cosmetically elegant. Antioxidants in the hydroquinone phase are instrumental in stabilizing the color of the hydroquinone composition. The most preferred example of such an antioxidant is sodium metabisulfite. Exceptional antioxidant qualities are seen at 0.10% (all percentages in the application are weight percent) and above, preferably from about 0.05% to about 0.5% for sodium metabisulfite.

Also in this embodiment is a cationic salt of acidic ascorbyl esters, which further helps to maintain the acceptable color desired in the hydroquinone composition. Cationic salts of acidic ascorbyl esters, including inorganic salts, preferably magnesium ascorbyl phosphate, and amino acyl derivatives, preferably aminopropyl ascorbyl phosphate, are preferred in this invention.

Magnesium ascorbyl phosphate (also called magnesium ascorbityl phosphate or magnesium L-ascorbyl-2-phosphate) has a chemical formula of $C_6H_6O_9P$-3/2 Mg. Magnesium ascorbyl phosphate has been available as an antioxidant and a melanin inhibitor for use in formulations of pH about 7.0 to 8.5. Hydroquinone has been used in compositions of a pH of about 2.0 to 4.0. In this invention, hydroquinone and magnesium ascorbyl phosphate may be used in neutral pH ranges without exhibiting excessive discoloration preferably for greater than about six months, more preferably for greater than about twelve months, and most preferably for greater than about eighteen months, or physical instability. The amount of magnesium ascorbyl phosphate is this embodiment of the invention is about 0.25% to about 3%, preferably about 0.25% to about 1%, most preferably at least about 0.5%.

In another embodiment, sodium metabisulfite and magnesium ascorbyl phosphate are used in about 0.01% (preferably from about 0.05% to about 0.5%, most preferably at least about 0.1%,) and about 0.5% (preferably from about 0.25% to about 3%, more preferably from about 0.25% to about 1%, and most preferably at least about 0.5%) respectively in a composition with about 4% hydroquinone. Although about 0.01% sodium metabisulfite without magnesium ascorbyl phosphate may not color stabilize an about 4% hydroquinone composition, and about 0.5% magnesium ascorbyl phosphate without sodium metabisulfite may not either, the combination of sodium metabisulfite and magnesium ascorbyl phosphate in these percentages is effective to stabilize the color of the about 1% to about 12%, about 2% to about 10%, preferably about 2% to about 8% and more preferably about 3% to about 4% and most preferably 4% hydroquinone composition.

In another embodiment of the invention, hydroquinone and a protected retinoid are both combined in the composition. Retinoids, in particular retinoic acid, retinal, and their derivatives, isomers and analogs (such as adapalene, tazarotene and isotretoin), are beneficial for improving rough skin texture, mottled pigmentation, sallow complexion, lines and wrinkles. Forms of retinoids have been developed wherein the retinoid is protected by a protective system. The protective system can be an entrapment system, a single or multi-laminar system, such as by formation of vesicle, such as a liposome, or by utilizing wax, paraffin, silicone, polyethylene or any material or system which protects the retinoid from oxidation. The preferred protected retinoid is in the form of small beads or vesicles which are of a form that can be adjusted to be incorporated into varied topical compositions. One skilled in the art is familiar with the known protective system technologies, such as encapsulation and entrapment methodologies. A preferred embodiment utilizes encapsulation. For use herein, the encapsulation forms a protective system to prohibit or inhibit the oxidation of the retinoid. As utilized herein, the inhibition of the retinoid oxidation should be sufficient to prohibit browning of the composition for its shelf life, preferably greater than about six months, more preferably greater than about twelve months, and most preferably greater than about eighteen months. Examples of suitable methods of encapsulation include encapsulation by liposomes, wax, paraffin or any material or combination of materials which protect the retinoid from exposure to oxygen and inhibit oxidation of the retinoid from oxidation. Preferably, the protected retinoid, in particular retinoic acid, retinal, and their derivatives, isomers and analogs (such as adapalene, tazarotene and isotretoin), is in the form of small beads or spheres suitable for incorporation into a topical composition. The preferred form of protected retinol is manufactured by SunSmart (also known as Particle Sciences, Inc. of Bethlehem, Pa.) under the brand name of SunCaps A-1283. Retinoids are included from about 0.01% to about 5%, preferably from about 0.025% to about 2%, more preferably 0.05% to about 1.0%, and most preferably from about 0.025% to about 0.5%.

The color stability of the hydroquinone composition is promoted by one or more antioxidants in the hydroquinone phase, preferably sulfite, including but not limited to sulfites, bisulfites, metabisulfites, their salts and their derivatives, most preferably sodium metabisulfite, and a cationic salt of acidic ascorbyl esters, most preferably magnesium ascorbyl phosphate. While the hydroquinone is effective for the pigmentation disorder treatment, retinoid is used for its skin treatment benefits.

Compositions according to this invention may include dermatologically acceptable carriers. Such carriers are widely known in the art and deliver the composition's ingredients to the skin without excessive degradation, inactivation or other unwanted interaction. An acceptable carrier also possesses suitable aesthetic and cosmetic qualities and may include emollients, conditioners and the like. Compositions according to this invention may include additives or components to enhance the skin penetration of its ingredients. They may also include ingredients with other therapeutic actions, such as anti-inflammatories, antibiotics, exfoliants and peels.

Sodium Metabisulfite Concentration Testing

Tests, which results are detailed in the following two tables, are performed to show how well sodium metabisulfite ("SMBS") stabilizes color at each pH at 5° C. and 40° C. in 4% hydroquinone ("HQ") compositions.

TABLE I

Color Stability of 4% HQ Compositions with varying pH and % Sodium Metabisulfite at 5° C. and 40° C.
Result of pH-VS-SMBS Concentration

| pH/SMBS % | 3.50 | 4.00 | 4.50 | 5.00 | 5.50 | 6.00 | 6.50 | 7.00 |
|---|---|---|---|---|---|---|---|---|
| | | | | 5° C. | | | | |
| 0.00 | 3 | 3 | 3 | 3 | 4 | 5 | 8 | 9 |
| 0.01 | 0 | 0 | 0 | 0 | 0 | 2 | 5 | 8 |
| 0.05 | 0 | 0 | 0 | 0 | 0 | 0 | 0 | 0 |
| 0.10 | 0 | 0 | 0 | 0 | 0 | 0 | 0 | 0 |
| 0.15 | 0 | 0 | 0 | 0 | 0 | 0 | 0 | 0 |
| 0.20 | 0 | 0 | 0 | 0 | 0 | 0 | 0 | 0 |
| 0.25 | 0 | 0 | 0 | 0 | 0 | 0 | 0 | 0 |

TABLE I-continued

Color Stability of 4% HQ Compositions with varying pH and % Sodium Metabisulfite at 5° C. and 40° C.
Result of pH-VS-SMBS Concentration

| pH/SMBS % | 3.50 | 4.00 | 4.50 | 5.00 | 5.50 | 6.00 | 6.50 | 7.00 |
|---|---|---|---|---|---|---|---|---|
| | | | | 40° C. | | | | |
| 0.00 | 7 | 7 | 7 | 8 | 8 | 8 | 9 | 10 |
| 0.01 | 0 | 0 | 5 | 6 | 7 | 7 | 9 | 9 |
| 0.05 | 0 | 0 | 0 | 0 | 0 | 0 | 4 | 0 |
| 0.10 | 0 | 0 | 0 | 0 | 0 | 0 | 0 | 0 |
| 0.15 | 0 | 0 | 0 | 0 | 0 | 0 | 0 | 0 |
| 0.20 | 0 | 0 | 0 | 0 | 0 | 0 | 0 | 0 |
| 0.25 | 0 | 0 | 0 | 0 | 0 | 0 | 0 | 0 |

Color Scale Legend
0 water white (no color)
1 extremely light straw (only a slight variation from water white)
2 light straw yellow
3 medium straw yellow
4 draw straw yellow
5 light amber
6 medium amber
7 dark amber
8 light brown
9 medium brown
10 dark brown Table I shows that at 5° C., 4% hydroquinone compositions maintain their white color with the addition of at least about 0.01% sodium metabisulfite at the low pH ranges (from about 3.50 to about 5.50) and at least 0.05% sodium metabisulfite for pH about 6.0 to about 7.0.

At 40° C., 4% hydroquinone compositions have the same color stability with slightly more sodium metabisulfite, at least about 0.01% at about 3.5 to about 4.0 pH; at least about 0.05% sodium metabisulfite at about 4.5 to about 6.0 pH; and at least about 0.10% sodium metabisulfite at about 6.5 to about 7.0 pH.

Magnesium Ascorbyl Phosphate Concentration Testing

Tests, which results are detailed in the following two tables, are performed at 5° C. and 40° C. for certain percentages of magnesium ascorbyl phosphate at specific pHs. An improvement in the color stability of the 4% hydroquinone compositions is seen at and above 2.0% magnesium ascorbyl phosphate in the 6–7 pH range.

TABLE II

Color Stability of 4% HQ Compositions with varying pH and % Magnesium Ascorbyl Phosphate at 5° C. and 40° C.
Result of pH-VS-MAP Concentration

| pH/MAP % | 3.50 | 4.00 | 4.50 | 5.00 | 5.50 | 6.00 | 6.50 | 7.00 |
|---|---|---|---|---|---|---|---|---|
| | | | | 5° C. | | | | |
| 0.0 | 3 | 3 | 3 | 4 | 4 | 5 | 8 | 9 |
| 0.5 | 1 | 2 | 2 | 2 | 2 | 3 | 4 | 3 |
| 1.0 | 1 | 2 | 2 | 2 | 2 | 3 | 3 | 2 |
| 1.5 | 1 | 2 | 2 | 3 | 3 | 4 | 3 | 2 |
| 2.0 | 1 | 2 | 2 | 3 | 3 | 4 | 3 | 2 |
| 2.5 | 0 | 2 | 2 | 3 | 4 | 4 | 3 | 3 |
| 3.0 | 0 | 2 | 2 | 3 | 4 | 4 | 3 | 3 |
| | | | | 40° C. | | | | |
| 0.0 | 7 | 7 | 7 | 8 | 8 | 8 | 9 | 10 |
| 0.5 | 7 | 7 | 7 | 7 | 8 | 8 | 7 | 7 |
| 1.0 | 6 | 7 | 7 | 7 | 6 | 7 | 6 | 6 |
| 1.5 | 6 | 7 | 7 | 7 | 7 | 5 | 5 | 5 |

TABLE II-continued

Color Stability of 4% HQ Compositions with varying pH
and % Magnesium Ascorbyl Phosphate at 5° C. and 40° C.
Result of pH-VS-MAP Concentration

| pH/MAP % | 3.50 | 4.00 | 4.50 | 5.00 | 5.50 | 6.00 | 6.50 | 7.00 |
|---|---|---|---|---|---|---|---|---|
| 2.0 | 4 | 5 | 5 | 7 | 5 | 5 | 4 | 4 |
| 2.5 | 4 | 6 | 6 | 7 | 5 | 5 | 4 | 4 |
| 3.0 | 4 | 5 | 6 | 6 | 4 | 5 | 4 | 4 |

Color Scale Legend
0 water white (no color)
1 extremely light straw (only a slight variation from water white)
2 light straw yellow
3 medium straw yellow
4 dark straw yellow
5 light amber
6 medium amber
7 dark amber
8 light brown
9 medium brown
10 dark brown Table II shows that at 5° C., 4% hydroquinone compositions maintain their white or light straw color with the addition of at least about 0.5% magnesium ascorbyl phosphate at the low pH ranges (from about 3.50 to about 5.50) and when about 1.0 to about 2.0% magnesium ascorbyl phosphate is used in the pH range of about 7.0. Color stability improvement is evident at all levels. 0.5% magnesium ascorbyl phosphate protected at pH 6.0–7.0, 1.0–1.5% at pH 5.5–7.0, and 2.0–3.0% at pH 3.5–7.0.

At 40° C., 4% hydroquinone compositions are more likely to excessively discolor and magnesium ascorbyl phosphate helps to stabilize the color, by preventing the brownish black discoloration and maintaining an amber color. This is seen at about a pH of 3.50 with at least about 2.0% magnesium ascorbyl phosphate, and again at a pH of about 6.5 to about 7.0 with at least about 2.0% magnesium ascorbyl phosphate.

EXAMPLE 1

A specific embodiment of the invention is listed in the following table. The composition is preferably formulated in separate phases as designated below.

| Trade Name | CTFA Name | Percent |
|---|---|---|
| PHASE A | | |
| Purified Water | Purified Water | 45.07 |
| PHASE B | | |
| Carbomer 940 | Carbomer | 0.03 |
| Disodium EDTA | Disodium EDTA | 0.10 |
| Sodium Citrate | Sodium Citrate | 0.18 |
| PHASE C | | |
| Lecinol S-10 | Hydrogenated Lecithin | 0.75 |
| PHASE D | | |
| Phenyl Trimethicone | Phenyl Trimethicone | 4.00 |
| Gransil GCM-5 | Cyclopentasiloxane, Polysilicone-11 | 2.50 |
| CK-100 | Dimethiconol | 0.39 |
| PHASE E | | |
| Linoleic Acid | Linoleic Acid | 2.50 |
| Cetyl alcohol | Cetyl alcohol | 2.75 |
| Lipomulse 165 | Glyceryl Stearate (and) PEG-100 Stearate | 3.20 |
| Cosmowax J | Cetearyl Alcohol (and) Ceteareth | 1.50 |

-continued

| Trade Name | CTFA Name | Percent |
|---|---|---|
| BHT | Butylated Hydroxytoluene | 0.05 |
| Vitamin E Acetate | Tocopheryl Acetate | 0.75 |
| PHASE F | | |
| Sepigel 305 | Polyacrylamide (and) C 13–14 isoparaffin (and) laureth-7 | 1.75 |
| PHASE G | | |
| Purified Water | Purified Water | 2.00 |
| Sodium Metabisulfite | Sodium Metabisulfite | 0.25 |
| PHASE H | | |
| Purified Water | Purified Water | 3.00 |
| VC-PMGU | Magnesium L-Ascorbyl Phosphate | 0.50 |
| PHASE I | | |
| Purified Water | Purified Water | 5.00 |
| Alcohol SDA 40, 200 Proof | Alcohol | 3.00 |
| Glycerin 99% USP | Glycerin 99% USP | 4.00 |
| Hydroquinone | Hydroquinone | 4.00 |
| PHASE J | | |
| Purified Water | Purified Water | 1.00 |
| Triethanolamine 99% | Triethanolamine 99% | 0.60 |
| PHASE K | | |
| Benzyl alcohol | Benzyl Alcohol | 0.50 |
| Fragrance MAIDA J-9145 | Fragrance | 0.03 |
| Phenoxetol | Phenoxyethanol | 0.60 |
| PHASE L | | |
| Suncaps A-1283 | Water, Soybean (Glycine Soja) Oil, Carnauba (Copernicia Cerifera), wax, tocopherol, retinol, Ceteareth-20 | 10.00 |

EXAMPLE 2

These phases (described below) are combined in a mixing tank with an in-line homogenizer as follows. Phase A is added to the tank, which is held at a temperature of from about 70° to about 75° C., and in which a $CO_2$ atmosphere is maintained. Phase B is added, and mixing is initiated. Phase C is added and the homogenizer is engaged. Phase D is heated to from about 70° to about 75° C. in a separate vessel with mixing until a clear, uniform phase is obtained. Phase D is then added to the main vessel. Phase E is heated to from about 70° to about 75° C. in a separate vessel with mixing until a clear, uniform phase is obtained. Phase E is then added to the main vessel. Phase F is then added directly to the main vessel. The homogenizer is then disengaged and the vessel is cooled to about 50° C. Phase G is mixed in a separate vessel until clear, and then $CO_2$ is slowly introduced to the phase. Phase G is then added to the main vessel. Phase H is mixed in a separate vessel, and $CO_2$ is added to the phase before it is added to the main vessel. Phase I is then added directly to the main vessel. Phase J is premixed in a separate vessel with $CO_2$ and then added to the main vessel. The vessel is then cooled to about 25° to about 27° C. Phase K is premixed in a separate vessel with $CO_2$, and then added to the main vessel. Phase L is premixed in a separate vessel and then added to the main vessel. The finished product is introduced into a container that has been flooded with Argon gas and then sealed.

| Trade Name | CTFA Name | Percent |
|---|---|---|
| PHASE A | | |
| Purified Water | Purified Water | 45.25 |
| PHASE B | | |
| Carbomer 940 | Carbomer | 0.03 |
| Disodium EDTA | Disodium EDTA | 0.10 |
| PHASE C | | |
| Lecinol S-10 | Hydrogenated Lecithin | 0.75 |
| PHASE D | | |
| Phenyl Trimethicone | Phenyl Trimethicone | 4.00 |
| Gransil GCM-5 | Cyclopentasiloxane, Polysilicone-11 | 2.50 |
| CK-100 | Dimethiconol | 0.39 |
| PHASE E | | |
| Linoleic Acid | Linoleic Acid | 2.50 |
| Cetyl alcohol | Cetyl alcohol | 2.75 |
| Lipomulse 165 | Glyceryl Stearate (and) PEG-100 Stearate | 3.20 |
| Cosmowax J | Cetearyl Alcohol (and) Ceteareth | 1.50 |
| BHT | Butylated Hydroxytoluene | 0.05 |
| Vitamin E Acetate | Tocopheryl Acetate | 0.75 |
| PHASE F | | |
| Sepigel 305 | Polyacrylamide (and) C 13–14 isoparaffin (and) laureth-7 | 1.75 |
| PHASE G | | |
| Purified Water | Purified Water | 2.00 |
| Sodium Metabisulfite | Sodium Metabisulfite | 0.25 |
| PHASE H | | |
| Purified Water | Purified Water | 3.00 |
| VC-PMGU | Magnesium L-Ascorbyl Phosphate | 0.50 |
| PHASE I | | |
| Purified Water | Purified Water | 5.00 |
| Alcohol SDA 40, 200 Proof | Alcohol | 3.00 |
| Glycerin 99% USP | Glycerin 99% USP | 4.00 |
| Hydroquinone | Hydroquinone | 4.00 |
| PHASE J | | |
| Purified Water | Purified Water | 1.00 |
| Triethanolamine 99% | Triethanolamine 99% | 0.60 |
| PHASE K | | |
| Benzyl alcohol | Benzyl Alcohol | 0.50 |
| Fragrance MAIDA J-9145 | Fragrance | 0.03 |
| Phenoxetol | Phenoxyethanol | 0.60 |
| PHASE L | | |
| Suncaps A-1283 | Water, Soybean (Glycine Soja) Oil, Carnauba (Copernicia Cerifera), wax, tocopherol, retinol, Ceteareth-20 | 10.00 |

It is understood that while the invention has been described in conjunction with the detailed description thereof, that the foregoing description is intended to illustrate and not limit the scope of the invention, which is defined by the scope of the appended claims. Other aspects, advantages, and modifications are evident from a review of the following claims.

What is claimed is:

1. A method of stabilizing a hydroquinone composition having a pH of about 5.5 to about 8.0 comprising:
   adding a cationic salt of acidic ascorbyl esters.
2. The method of claim 1 wherein the pH is about 5.5 to about 7.5.
3. The method of claim 1 wherein the pH is about 6.0 to about 7.5.
4. The method of claim 1 wherein the hydroquinone is present in about 1 to about 12%.
5. The method of claim 1 wherein the hydroquinone is present in about 2 to about 10%.
6. The method of claim 1 wherein the hydroquinone is present in about 2 to about 8%.
7. The method of claim 1 wherein the hydroquinone is present in about 3 to about 4%.
8. The method of claim 1 wherein the hydroquinone is present in about 4%.
9. The method of claim 1 further comprising a water-soluble antioxidant.
10. The method of claim 9 wherein the antioxidant comprises sulfite.
11. The method of claim 9 wherein the antioxidant comprises sodium metabisulfite.
12. The method of claim 11 wherein the sodium metabisulfite is present in at least about 0.05%.
13. The method of claim 11 wherein the sodium metabisulfite is present at about 0.05% to about 0.5%.
14. The method of claim 1 wherein the cationic salt comprises an inorganic salt.
15. The method of claim 1 wherein the cationic salt comprises magnesium ascorbyl phosphate.
16. The method of claim 15 wherein the magnesium ascorbyl phosphate is present in at least about 0.1%.
17. The method of claim 15 wherein the magnesium ascorbyl phosphate is present at about 0.25 to about 3%.
18. The method of claim 15 wherein the magnesium ascorbyl phosphate is present at about 0.25 to about 1%.
19. The method of claim 9 wherein the antioxidant comprises sodium metabisulfite and the cationic salt comprises magnesium ascorbyl phosphate.
20. The method of claim 19 wherein the sodium metabisulfite is present in at least about 0.05% and the magnesium ascorbyl phosphate is present in at least about 0.5%.
21. The method of claim 1 wherein the cationic salt comprises an amino acyl derivative.
22. The method of claim 21 wherein the cationic salt comprises aminopropyl ascorbyl phosphate.
23. The method of claim 1 wherein the cationic salt comprises a sodium ascorbyl phosphate.

* * * * *